(12) United States Patent
Kumar

(10) Patent No.: US 11,877,584 B2
(45) Date of Patent: Jan. 23, 2024

(54) BUILDING RESILIENCE TO COVID-19 AND ITS VARIANTS

(71) Applicant: Kaplesh Kumar, Wellesley, MA (US)

(72) Inventor: Kaplesh Kumar, Wellesley, MA (US)

( * ) Notice: Subject to any disclaimer, the term of this patent is extended or adjusted under 35 U.S.C. 154(b) by 362 days.

(21) Appl. No.: 17/236,990

(22) Filed: Apr. 21, 2021

(65) Prior Publication Data

US 2021/0337854 A1  Nov. 4, 2021

Related U.S. Application Data

(60) Provisional application No. 63/016,820, filed on Apr. 28, 2020, provisional application No. 63/014,631, filed on Apr. 23, 2020.

(51) Int. Cl.
*A23L 33/00* (2016.01)
*G16H 20/30* (2018.01)

(52) U.S. Cl.
CPC .............. *A23L 33/30* (2016.08); *G16H 20/30* (2018.01)

(58) Field of Classification Search
CPC ................................ A23L 33/00; G16H 20/30
See application file for complete search history.

(56) References Cited

U.S. PATENT DOCUMENTS 9,603,857 B2 * 3/2017 Kumar ................. A61K 31/573

OTHER PUBLICATIONS 50 (2020 332-334 (first publ. online Mar. 31, 2020.*
Nizri et al. Technique in Coloprotology 2013; 18,145-149.*
Yamada et al. Clinica Chimia Acta 509 (2020)235-243.*
Nurshad Ali. Wiley J. Medical Virology 2020; 92;2409-2411.*
Jarvis S., How quickly do Covid-19 symptoms develop and how long do they last?, https://patient.info/news-and-features/coronavirus-how-quickly-do-covid-19-symptoms-develop . . . Feb. 2021.
Y. Ezzatvar et al, Physical Activity and Risk of Infection, Severity and Mortality of Covid-19: a Systematic Review and Non-Linear Dose-Resp . . . , Br.J.Sports Med 2022 (0) 1-7.

* cited by examiner

*Primary Examiner* — Shirley V Gembeh

(57) ABSTRACT

Method of building resistance to Covid-19 disease development. The strong link between the distribution of Covid-19 disease (CV) severity across the United States population and that of systemic inflammation, as indicated in the individual's C-reactive protein (CRP) level, explains the widely varied symptomatic responses of individuals afflicted with the virus. The data are consistent with the fewer infections and deaths reported for the Asian countries. The disease pathologies of CV and non-specific interstitial pneumonia (NSIP) patients bear close similarities. Modeling the disease as a chemically reactive process indicates that the virus catalyzes the inflammation driven reaction, causing lung infiltration and injury, up to and including patient death. Prevention methods involving exercise and diet successfully applied for lung stabilization in NSIP also apply to CV mitigation, the goal of which is to achieve pre-disease CRP levels of <10 mg/L, and preferably <3 mg/L, and more preferably <1 mg/L.

11 Claims, No Drawings

BUILDING RESILIENCE TO COVID-19 AND ITS VARIANTS

This nonprovisional patent application fully incorporates herein by reference in its entirety U.S. Provisional Patent Application No. 63/014,631 filed Apr. 23, 2020, and entitled CORONAVIRUS TREATMENT METHOD.

This application also fully incorporates herein by reference in its entirety U.S. Provisional Patent Application No. 63/016,820 filed Apr. 28, 2020, and entitled COVID-19 DISEASE MODELING AND TREATMENT.

This application is related to U.S. Pat. No. 10,052,336 B2 and U.S. Pat. No. 9,603,857 B2, both of which are fully incorporated herein in their entirety by reference.

FIELD OF INVENTION

This invention generally relates to methods of protecting individuals and society against the development of severe disease, and more particularly protecting against the development of severe Covid-19 disease caused by infection with the SARS-COV2 virus and its variants.

BACKGROUND OF INVENTION

The past year has seen federal and state authorities taking unprecedented steps in efforts to stem the rapid invasion of society by the SARS COV2 Coronavirus Covid-19 disease (CV) pandemic, which has resulted in over one-half million deaths across this vast homeland from the deadly Covid-10 disease. What has set this virus apart from others is that about half of the infected individuals remain asymptomatic, with little to no symptoms, but at the same time functioning as efficient carriers of the virus that can be transferred unknowingly to others through casual social contact.

Society's helplessness against the onslaught of this insidious disease forced it to initially try and limit Covid-19's spread with the wearing of face masks, restricting physical human interaction to separation distances in excess of six feet, mandating that people stay in their homes unless they were a medical first responder or performed an essential service, and quarantining for a period of fourteen days people who either came into contact with a known coronavirus-infected individual or arrived from a region where the virus was rampant. Those infected and experiencing fever and shortage of breath were typically admitted for monitoring and treatment in the hospital setting. Two to five days after onset, the symptoms of about twenty percent of the infected population, many of them senior citizens, worsened; they were then closely monitored, and a number of them (about five percent) eventually placed on ventilators. About two percent of the population did not survive from a SARS COV2 viral infection.

The efforts to limit the spread of the disease by isolating people and thereby "flatten the curve," so that the limited available treatment resources were able to manage the reduced (flattened curve) patient caseload, showed promise. However, many objected to the Government's guidelines and refused to wear masks or maintain their six feet separations from others, some in the belief that the virus was a hoax perpetrated by the Government, and others rebelling against what they perceived was an infringement of their freedom of choice under the Constitution. The mobility and social interactions of these groups, unfortunately, likely contributed to the multiple surges of new infections seen across many states following brief periods of stabilization, not only of the original SARS COV2 virus but also its several mutant variants that emerged. The limited gains that were achieved came at tremendous cost to society, economically, socially, and psychologically.

Coincidentally, Asian populations, for example, Chinese, Japanese, and South Koreans, have reportedly done appreciably better in managing the disease than have western populations which has made many question the veracity of the reported data for the Asian countries, particularly that from China where the virus reportedly originated.

With no known therapy, a number of approaches have been pursued. Studies aimed at combating the disease and preventing serious injury and death have included evaluating the efficacy of various available drugs (e.g, hydroxychloroquine, remdesivir, and gluco-corticosteriods) and developing a vaccine to target the virus. Some limited success was reported with the gluco-corticosteriod drug dexamethasone, an anti-inflammatory, which when administered to Covid-19 hospitalized patients on supplemental oxygen or on ventilators resulted in reducing the fatalities from the disease. Earlier, the patentee herein had predicted that the disease severity was dependent on the patient's preexisting level of inflammation (prior to disease onset), as measured by the concentration of C-Reactive Protein (CRP) in the patient's blood (See, e.g., U.S. Provisional Patent Applications No. 63/014,631 filed Apr. 23, 2020 and No. 63/016,820 filed Apr. 28, 2020, and paper entitled "Building Resilience to Covid-19 Disease Severity, J. Med. Res. Prac., Vol. 9(1), 1-7, 2020—published online 28 May 2020), a finding that was validated in several published papers (See, e.g., X. Luo et al "Prognostic Value of C-Reactive Protein in Patients With Coronavirus 2019," Clinical Infectious Diseases, published online 23 May 2020, DOI: 10.1093/cid/ciaa641; C. Tan et al, C-reactive protein correlates with computed tomographic findings and predicts severe COVID-19 early." J. Med. Virol., published online 25 Apr. 2020, DOI: 10.1002/jmv.25871).

In each of those published cases, the initial inflammation level was recorded upon the patient's admission at the medical facility for Covid-19 treatment, i.e., the patient was already infected with the virus, which raises the possibility that the infection may have contributed to some of the initial inflammation measured at admission. Nevertheless, the observation that the initial measured inflammation level has prognostic value in determining the course of disease severity of Covid-19 patients, and that subsequent increases in the CRP level of the patient during disease progression directly correlate with the degree of the patient's tissue degradation, when reconciled with the fact that more than half of those infected remain asymptomatic, leads to the inevitable conclusion that the asymptomatic carriers of the virus must have sufficiently low preexisting inflammation, preventing the disease from manifesting itself at a level necessary to develop the Covid-19 symptoms.

Fortunately, after almost a year of intensive efforts by a number of vaccine developers, several promising vaccines have been developed and are being injected into American arms. The US Federal Drug Administration (FDA) has granted Emergency Use Authorization (EUA) for vaccines developed by Pfizer BioNTech, Moderna, Johnson and Johnson (which is currently paused due to blood clotting reported in a small number of patients); similar approval may also be granted in due course to a fourth vaccine developed by Astra Zeneca. The authorized vaccines are reportedly about 90 percent effective against the original SARS COV2 virus in real world conditions. As of the date of this writing, more than 100 million Americans have been fully vaccinated and one-half of the population has received at least one dose of one of the FDA's EUA-approved vaccines. The vaccination effort continues in earnest.

Although vaccination using the FDA-approved vaccines has partly alleviated some of the concerns of the original Covid-19 virus, several more easily transmissible dangerous mutations of the original virus have emerged, the consequence of increased viral replication from multiply transferred infections among the population. Since many refuse to take the standard precautions of wearing masks, social distancing, and washing hands, it is easier for the virus to be transmitted from one to another, resulting in its increased multiple replication. The mutants have raised concerns that the vaccine may not be sufficiently effective against them, so efforts are continuing at developing additional vaccines for controlling the mutants. It is becoming clear that this will present a long-term evolving concern, and vaccine development or other treatment will need to keep pace with the coronavirus mutations. Consequently, supplemental therapies capable of mitigating the harsh effects of the disease from the emerging coronavirus mutations will be an ongoing need for protecting people during gaps in availability of vaccines tailored to mitigating new mutants as they emerge.

SUMMARY OF THE INVENTION

The severity of Covid-19 disease (CV) caused by the SARS COV2 coronavirus correlates closely with the distribution of systemic inflammation across the United States population. The strong link between the two underlies the varied symptomatic responses among patients afflicted with the virus, and explains the increased incidence among the African-American and Latin-American populations, and the fewer infections and deaths reported for the Asian countries.

Symptomatically and pathologically, the effects on human populations of Covid-19 (CV) and non-specific interstitial pneumonia (NSIP) bear close similarities. Disease modeling has concluded that the virus catalyzes the inflammation driven reaction, causing lung infiltration and injury, up to and including patient death. Successful prevention and intervention methods involving reducing systemic inflammation for lung stabilization in NSIP also apply to CV control; the goal of such prevention and intervention for Covid-19 is to achieve low inflammation levels corresponding to patient C-Reactive Protein (CRP) levels of <10 mg/L, and preferably <3 mg/L, and even more preferably <1 mg/L.

DETAILED DESCRIPTION OF THE INVENTION

Disease Symptoms and Pathology—Similarities of CV to NSIP

There is a close similarity of both the CV pathology, as revealed through Computed Tomography (CT) scans of the affected lungs, and the CV patients' reported symptoms following onset of the disease with what a non-specific interstitial pneumonitis (NSIP) afflicted patient experiences in the early stages of the NSIP lung disease: dry cough, fatigue/dyspnea (shortness of breath upon exertion), fever, chills, and normal white blood count.[2,3] (See, e.g., Han R., Huang L., Jiang H. et al, Early Clinical and CT Manifestation of Coronavirus Disease 2019 (Covid-19) Pneumonia, AJR 2020; 215: 1-6; Kumar K., Inflammatory Disease Model and Treatment Method, J. Med. R. Prac. 2013; 2: 120-126; U.S. Pat. No. 10,052,336 B2; U.S. Pat. No. 9,603, 857 B2) Both diseases are characterized by systemic and lung inflammation. As reported for CV patients, High Resolution Computed Tomography (HRCT) scans of the NSIP lungs too show ground glass opacity (GGO) in the lungs' peripheral basal regions.[4] (See, Kiligerman S. J., Groshong S, Brown K. K., and Lynch D. A., Non Specific Interstitial Pneumonia: Radiologic, Clinical, and Pathologic Considerations, Han et al's findings[2] from Computed Tomography (CT) scans of 108 early stage CV patients ranging in age from 21 to 90 years, with a mean age of 45 years, show patchy GGO lesions in 60 percent of the patients, distributed in the lung's peripheral zones across single or multiple lobes of the lung. The CT scans were performed within one to three days of onset of disease. Irreversible, fibrotic-type changes, permanently damaging the lung tissue, were not seen as the disease had not yet advanced in these patients to the severe stage. Significantly, they reported that 107 out of the 108 (or 99 percent) patients had elevated CRP values, although the authors did not report the actual values measured.

Lung Stabilization through Inflammation Reduction

The solution to controlling or mitigating the harsh CV effects would, thus, seem to be successful intervention of the CV-supported process that causes lung tissue injury within the context of the inflammatory process. An NSIP patient with elevated systemic inflammation was able to largely arrest continuing lung damage based on the treatment recommendations flowing from the inflammatory disease model presented below. The damaging biological inflammatory process, modeled as a chemically reactive process, predicted that inflammation reduction and control will arrest or slow down the process, impeding further lung injury.

A recent study had identified age and obesity as the critical factors favoring CV disease development, which led the researchers to suspect inflammation as a factor in advancing the disease. (https://www.zdnet.com/article/nyu-scientists-largest-u-s-study-of-covid-19-finds-obesity-the-single-biggest-factor-in-new-york-critical-cases/). Earlier, too, it had been noted that obesity (and other risk factors) correlated well with increased systemic inflammation, and that inflammation increased with age-ascribing the increased inflammation among the elderly as responsible for the increased incidence of age related diseases in that population segment. (Kumar K., Inflammatory Disease Model and Treatment Method, J. Med. R. Prac. 2013; 2: 120-126) The reported evidence to date, as discussed below, shows that such a correlation also applies to the higher incidence of serious CV illness in the elderly.

Disease Model

The abnormal biological process causing the disease, when modeled as a chemically reactive process, allows the examination of the significance of inflammation in diseases marked with systemic inflammation, based on the following chemical reaction:

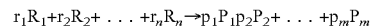

$$r_1R_1 + r_2R_2 + \ldots + r_nR_n \rightarrow p_1P_1p_2P_2 + \ldots + p_mP_m$$

where $r_1, \ldots r_n$ are the number of moles respectively of reactants $R_1, \ldots R_n$;

$p_1, \ldots, p_m$ are the number of moles respectively of products $P_1, \ldots P_m$; and n and m are respectively the number of reactants and products.

Since the reactants in the above reaction model combine in specific proportions to produce products (which also form in specific proportions among themselves), if inflammation (i.e. one of the proteins or other biological species) associated with disease appears as a reactant, R, a reduction in its quantity will lead to less consumption of the other reactant(s) and, consequently, less progression of the disease. Conversely, if systemic inflammation is the result of the underlying disease, i.e. it is a product of the reaction, then a low inflammation level means that less of the other products are also formed, or, in other words, less of the reactant species are consumed—again pointing to an arresting or slowing down of the disease.

A third possible role of inflammation is that of a catalyst. Where the activation energy for the reaction causing the underlying disease may be high in the absence of medically significant inflammation, thereby inhibiting disease, increasing inflammation could provide alternate lower activation energy pathways for such reactions, allowing the disease to propagate more rapidly to the patient's detriment because of increased disease reaction rate(s). That lowered activation energy, as further modulated and lowered additionally by the virus, seems to be in operation here, as discussed later.

In each of the above three roles that inflammation could play in disease progression, the model concludes that inflammation reduction would lead to an arresting or slowing down of the disease. The Patient X in U.S. Pat. No. 10,052,336 B2 and U.S. Pat. No. 9,603,857 B2 was accordingly able to control progression of his NSIP lung disease by reducing the systemic inflammation to below 3 mg/L through exercise, supplemented with an anti-inflammatory diet.[3]

Analysis

The above disease model is useful to analyze the additional role played by CV-infected cells in promoting accelerated lung damage. A key observation in this regard is that for CV infected individuals there is less than a twenty percent chance that the disease will mature to the point where hospitalization may be required and less than a five percent chance that ventilator support will be needed. As discussed earlier, high inflammation, as measured by the patients' CRP values, is observed universally in almost all CV patients, which establishes a close correlation between the disease and the systemic inflammation present. (For reference, it may be noted that Patient X in Reference 3 was able to largely arrest NSIP disease by driving down the inflammation with exercise and anti-inflammatory diet control to 1-3 mg/L and less.)

It is, therefore, instructive to examine the CRP distribution across the population to assess how closely it correlates with the distribution of CV disease severity. The CRP distribution across the Caucasian population in the 40 to 84 years age group with no history of cardiovascular disease was reported to have a median CRP value of about 1.5 mg/L, with a quarter of the sample group in the 3.2-3.48 mg/L range, and less than 5 percent >10 mg/L.[9] (CRP distributions of African American and Latin American minorities and individuals with significant underlying medical issues will likely skew this distribution to higher CRP values in view of their known enhanced risk factors, such as obesity and hypertension.)

The above values correlate well with the 80 percent of CV patients experiencing none to mild symptoms, 20 percent developing moderate to severe symptoms, and less than 5 percent requiring ventilator support, thereby confirming that the disease and its severity is largely determined by the degree of systemic inflammation present. The kinetics of the lung injury due to disease, as discussed below, however, is believed to be determined by the virus-modulated value of the activation energy for the reaction.

The CRP distributions among the Chinese population and other similar Asian populations, including Japanese (and possibly South Korean), are shifted to lower CRP values compared to the CRP distributions of the western countries.

(Zhao Y., Wang R., Yan X., Distribution of C-Reactive Protein and Its Association with Cardiovascular Risk Factors in a Population-Based Sample of Chinese, Disease Markers 2010; 28:333-342) The mean age of those sampled was 47.8 years and the mean measured CRP was 0.55 mg/L, much lower than the 1.52 mg/L median value reported of the Caucasian population. Sixty-five percent Chinese had CRP <1 mg/L, and only 1.3 percent showed values over 10 mg/L. These data strongly support the conclusion that the Chinese and other Asian populations, on average, will exhibit greater resilience to CV infection than Caucasians and also, on average, suffer from milder forms of the disease with fewer deaths. The foregoing lends credence to Chinese, Japanese, and South Korean claims of having suffered fewer CV related deaths than the United States and other western countries.

Since the pathologies of NSIP and CV affected lungs bear strong similarities, it is reasonable to conclude that the mechanisms that bring about the lung structural changes in both cases are likely similar, if not identical, for the two diseases. From the earlier NSIP findings, it is clear that inflammation plays the dominant role in allowing these processes to take place. Where significant systemic inflammation is suppressed to an acceptable level with exercise and an anti-inflammatory diet, further progression of the NSIP disease resulting in lung injury was shown to have been avoided or slowed. Exercise, four to five days weekly, both aerobic and resistance, has been shown in a number of studies to reduce systemic inflammation and measured CRP levels. A few months of 100-300 cumulative minutes per week of aerobic exercise on the treadmill or a stationary exercise bike, each session lasting 20 to 60 minutes, or resistance exercise including without limitation weight training for similar periods have been shown to be sufficient for reducing the CRP value to the <3 mg/L range. Swimming or Yoga will likely also achieve similar results. Anti-inflammatory diets, based on foods rich in antioxidants and anti-inflammatory compounds, include without limitation nuts (peanuts, almonds, and walnuts) and brightly and variedly colored fruits and vegetables, turmeric, and ginger.

The CV data, likewise, is consistent with high systemic inflammation being a prerequisite for serious disease progression and lung injury. (Han R., Huang L., Jiang H. et al, Early Clinical and CT Manifestation of Coronavirus Disease 2019 (Covid-19) Pneumonia, AJR 2020; 215:1-6; Kumar K., Inflammatory Disease Model and Treatment Method, JMRP 2013; 2: 120-126) The different responses and survivability of CV patients reporting varied symptoms like shortness of breath must, therefore, be related to the level of systemic inflammation present. The possibility that CV causes lung inflammation irrespective of systemic inflammation is further discounted as eighty percent of the patient population suffer only mild symptoms from the disease. Indeed, about half remain unaware of the infection, whereas if CV were the principal and independent cause of the observed lung inflammation, then the entire patient population afflicted by the disease, and not just twenty percent, would be expected to experience lung inflammation and its common symptoms of dry cough and shortness of breath.

The difference between the two diseases, however, is in the much more rapid rate of disease progression in CV patients versus NSIP patients. Since the basic lung injury mechanisms appear to be similar for both diseases, the trigger is likely also the same i.e., systemic inflammation lowering of the activation energy barrier to lung injury, and in the case of CV, further modulated to an even lower activation energy level by the virus acting as a catalyst, and resulting in the rapid disease progression rate observed for CV patients. The virus likely combines synergistically with the systemic inflammatory process to provide the even lower activation energy reaction pathways than would otherwise be present based on systemic inflammation alone.

Since about eighty percent of the infected individuals are asymptomatic or have mild flu-like symptoms, and given that the virus rapidly replicates numerous copies of itself upon association with the lung cell, the vast majority of the population would appear to have low enough acceptable levels of systemic inflammation so that the activation energy barrier remains sufficiently high even in the presence of the virus. This, in turn, suggests that the catalyzing effect of the CV-infected cell becomes operative mainly in the presence of sufficiently elevated medically significant inflammation. This further reinforces the conclusion that inflammation reduction should be a main focus of any non-vaccine CV therapy.

Since systemic inflammation corresponding to a C-Reactive Protein (CRP) level of <1 mg/L in the blood has been correlated with the lowest risk of heart disease, which is the most prevalent of all diseases, it would appear to be a good aspirational goal for any inflammation reduction therapy in the context of the CV disease. The CRP value should not preferably exceed 3 mg/L, the average risk for heart disease, which has been shown to be successful in slowing down the NSIP disease, or less preferably not exceed 10 mg/L. Less than five percent of the apparently healthy U.S. caucasian population has CRP levels over about 10 mg/L. (Nader R., Ridker P. M., Population Distributions of C-reactive Protein in Apparently Healthy Men and Women in the United States: Implication for Clinical Interpretation, Clinical Chemistry 2003, 49:666-669) This number is consistent with the roughly five percent of CV cases requiring ventilator support of which two to three percent do not survive. While CRP levels of 10 mg/L appear sufficient to survive the harshest effects of CV, based on the NSIP experience, however, inflammation reduction to less than 3 mg/L and more preferably <1 mg/L of CRP concentration would provide for milder effects.

Various ways to reduce the systemic inflammation have been discussed in U.S. Pat. No. 10,052,336 B2 and U.S. Pat. No. 9,603,857 B2. Of these, as discussed above, exercise alone, or preferably exercise supported with a diet rich in antioxidants and anti-inflammatory compounds, has been found to successfully reduce inflammation to CRP levels in the range of 1-3 mg/L or less. The quantum of required exercise is one that results in achieving the desired CRP goal value. The reported success with NSIP and the above discussion support the conclusion that by controlling inflammation to levels corresponding to CRP levels of <10 mg/L, or preferably <3 mg/L, or more preferably <1 mg/L, one should be able to largely mitigate the processes resulting in lung damage from the CV disease and limit its effects, at most, to mild flu-like symptoms during the time that the virus remains active in the body.

Immunosuppressant drugs can also be used for controlling the preexisting systemic inflammation to render partial immunity to disease, but they all notoriously have undesired side effects and are not acceptable as long-term solutions for otherwise healthy people. Besides, unlike drugs, exercise also keeps the lungs clear of mucous and other debris, thus, additionally limiting any potential alveolar damage. As demonstrated with the dexamethasone, immunosuppressant drugs may offer some partial relief by inflammation reduction to those at an advanced stage of the disease since increasing CRP levels has been shown to indicate increased tissue degradation; consequently, inflammation reduction should result in reduced tissue damage, which, in turn, translates to less severe disease. Unfortunately, since the disease worsens rapidly in a matter of days upon infection, exercise and diet no longer remain viable options for reducing the inflammation and other means, including drugs such as dexamethasone, must be employed.

If the anti-inflammatory exercise and diet regimen proposed herein, and as further elaborated upon in Reference 3, were followed, it is highly likely that the citizenry could effectively reduce their CRP levels below 10 mg/L, 3 mg/L, or <1 mg/L and develop sufficient immunity against the deathly aspects of the CV disease and its mutations. The increased immunity would also better position one to handle the SARS COV2 virus and its mutants upon any subsequent exposure. The scope of the instant invention is to be limited only by the claims and not by the description herein.

I claim:

1. A method for building a person's resilience to coronavirus comprising the steps of:

confirming that the person's preexisting C-Reactive Protein concentration in the blood prior to disease onset is more than 10 mg/L;

reducing the CRP concentration to less than 10 mg/L using non-toxic therapy selected from the group consisting of exercise, anti-inflammatory diet, and combinations thereof.

2. The method of claim 1, wherein said exercise includes aerobic exercise.

3. The method of claim 2, wherein aerobic exercise includes exercising on a treadmill.

4. The method of claim 2, wherein aerobic exercise includes exercising on a treadmill.

5. The method of claim 1, wherein exercise includes resistance exercise.

6. The method of claim 1, wherein anti-inflammatory diet includes antioxidants.

7. The method of claim 1, wherein anti-inflammatory diet includes diets selected from the group consisting of nuts, fruits, vegetables, turmeric, ginger, green tea, fish, flaxseed, and combinations thereof.

8. A method for building a person's resilience to coronavirus comprising the steps of:

confirming that the person's preexisting C-Reactive Protein concentration in the blood prior to disease onset is more than 3 mg/L;

reducing the CRP concentration to less than 3 mg/L using non-toxic therapy selected from the group consisting of exercise, anti-inflammatory diet, and combinations thereof.

9. The method of claim 8, wherein exercise includes aerobic exercise.

10. The method of claim 8, wherein anti-inflammatory diet includes antioxidants.

11. The method of claim 8, wherein anti-inflammatory diet includes diets selected from the group consisting of nuts, fruits, vegetables, turmeric, ginger, green tea, fish, flaxseed, and combinations thereof.

* * * * *